United States Patent [19]
Roberts et al.

[11] Patent Number: 5,750,141
[45] Date of Patent: May 12, 1998

[54] ADMINISTRATION OF VASO-ACTIVE AGENT AND THERAPEUTIC AGENT

[75] Inventors: Michael Stephen Roberts, Westlake; Sheree Elizabeth Cross, Tarragindi, both of Australia; Parminder Singh, Sussern, N.Y.

[73] Assignee: The University of Queensland, Queensland, Australia

[21] Appl. No.: 535,270

[22] PCT Filed: Apr. 8, 1994

[86] PCT No.: PCT/AU94/00174

§ 371 Date: Dec. 4, 1995

§ 102(e) Date: Dec. 4, 1995

[87] PCT Pub. No.: WO94/23748

PCT Pub. Date: Oct. 27, 1994

[30] Foreign Application Priority Data

Apr. 8, 1993 [AU] Australia .................. PL8224
Nov. 10, 1993 [AU] Australia .................. PM2306

[51] Int. Cl.⁶ ................................ A61F 13/00
[52] U.S. Cl. ............. 424/449; 514/944; 514/945; 514/969
[58] Field of Search ............. 424/449; 514/944, 514/945, 969

[56] References Cited

U.S. PATENT DOCUMENTS

| | | | |
|---|---|---|---|
| 3,551,554 | 12/1970 | Herschler | 424/9.4 |
| 3,832,460 | 8/1974 | Kosti | 424/54 |
| 4,055,660 | 10/1977 | Meierhenry | 514/535 |
| 4,379,792 | 4/1983 | Blaine | 514/369 |
| 4,514,384 | 4/1985 | Gallina | 514/179 |

FOREIGN PATENT DOCUMENTS

| | | |
|---|---|---|
| 40155/85 | 10/1985 | Australia . |
| 41200/85 | 11/1985 | Australia . |
| 31520/89 | 9/1989 | Australia . |
| 72700/91 | 9/1991 | Australia . |
| 338173 | 10/1989 | European Pat. Off. . |
| 448299 | 9/1991 | European Pat. Off. . |
| 449463 | 10/1991 | European Pat. Off. . |
| 57-73233 | 5/1982 | Japan . |
| 62-47592 | 3/1987 | Japan . |
| 64-64034 | 3/1989 | Japan . |
| 3-11017 | 1/1991 | Japan . |
| 3-83925 | 4/1991 | Japan . |
| 4-30083 | 2/1992 | Japan . |
| 4-243827 | 8/1992 | Japan . |
| 1277601 | 6/1972 | United Kingdom . |
| 1338172 | 11/1973 | United Kingdom . |
| 2192539 | 1/1988 | United Kingdom . |
| 89/00848 | 2/1989 | WIPO . |
| 91/01624 | 2/1991 | WIPO . |
| 92/15332 | 9/1992 | WIPO . |

OTHER PUBLICATIONS

Benedittis et al., *Pain.* 48:383–390, 1992.
Levy et al., *N. Eng. J. Med.*, 324: 776–777, 1991.
Rumsfield et al., *Annals Pharmacother.* 25:381–387, 1991.
Singh et al., *J. Pharm. Sci.*, 82:127–131, 1993.
Burnette et al., *J. Pharm. Sci.*, 77:132–137, 1988.
Masada et al., *Int. J. Pharm.*, 49: 57–62, 1989.
Singh et al., *Drug Design and Delivery*, 4:1–12, 1989.
Garagiola et al., *Clin. Ther.* 10:553–558, 1988.
Patent Joernaal, Abstract of ZA 90/6583, Sep. 1991.

*Primary Examiner*—D. Gabrielle Phelan
*Attorney, Agent, or Firm*—Knobbe, Martens, Olson & Bear, LLP

[57] ABSTRACT

A vaso-active agent is administered in combination with a therapeutic agent which is useful in treatment of tissue of the body which is located below the stratum corneum or the outermost layer of the epidermis, wherein the vaso-active agent may be administered by a local, topical or transdermal route to a particular site and the therapeutic agent may be administered in a similar manner in combination with the vaso-active agent or may be administered separately, wherein the vaso-active agent and the therapeutic agent for topical and/or transdermal administration may be provided in the form of a composition so as to increase local perfusion and/or concentration of the therapeutic agent at or adjacent an administration site of the vaso-active agent.

24 Claims, 13 Drawing Sheets

ADMINISTRATION OF VASO-ACTIVE AGENT AND THERAPEUTIC AGENT

FIELD OF INVENTION

This invention is a 371 of PCT/AU94/00174, filed Apr. 8, 1994.

THIS INVENTION relates to administration of a vaso-active agent in combination with a therapeutic agent which is useful in treatment of tissues of the body which are located below the stratum corneum or the outermost layer of the epidermis. The vaso-active agent may be administered by a local, topical or transdermal route to a particular site and the therapeutic agent may be administered in a similar manner in combination with the vaso-active agent or may be administered separately.

BACKGROUND ART

The transdermal route of administration has been investigated for a wide variety of active agents such as drugs since this route bypasses the gastrointestinal tract as a site of absorption and hence first pass degradation of the drug. Transdermal absorption ensures essentially constant administration of the drug and requires little motivation on the part of the patient. Reference to a variety of transdermal treatment systems is described in U.K. Specification 2192539 which refers to topical pharmaceutical compositions comprising the anti-inflammatory drug diclofenac or a salt thereof which uses as a vehicle a mineral oil. These compositions are described as having excellent skin penetration properties and which therefore can be used in transdermal therapeutic systems as a drug reservoir. The preferred mineral oil referred to in the specification is a liquid paraffin at body temperature which may be mixtures of saturated aliphatic or cycloaliphatic hydrocarbons.

The transdermal systems utilised in this specification included (i) a porous sintered polypropylene disc affixed to a polyester sheet, (ii) a sachet filled with a liquid composition of the invention and applied to the skin by a medicinal plaster, (iii) a finely divided composition as described above pressed to a sheet covered on one side with a polyester backing layer and on the other with siliconised polyester which is to be removed before use. Transdermal systems are cut from these laminates, and (iv) a laminated reservoir containing the compositions of the invention and control membrane together with a contact adhesive surface and a peel strip. Transdermal systems are cut from this laminate.

The skin is the major barrier to the entry of foreign solutes from the environment into the body as well to the loss of heat and moisture from the body. Appropriately formulated drugs with desirable physical chemical properties are absorbed through the skin and, indeed, drugs have been applied to the skin for the treatment of local disorders for many centuries. In recent years, a number of commercial products providing a controlled systemic delivery of drugs have been developed for a number of medical conditions (e.g. nitroglycerine, oestrogen and fentanyl patches). Products applied to the skin allow ready application and removal and are often referred to as topical delivery systems. The outermost layer of the epidermis, the stratum corneum, is normally assumed to be the major barrier to drug absorption through the skin. It has also been assumed that the drugs penetrating the epidermis are then removed by the dermal blood supply.

To date, topical drug delivery appears to be particularly useful in the management of local painful conditions with clinical studies being reported for pain arising from musculo-skeletal disorders, acute herpetic and post-herpetic neuralgia. Many of the therapies appear somewhat empirical in their approach to product formulation as reported in Benedittus et. al. (1992) Pain 48 383–390 or controversial as discussed in Levy et al. N Eng J Med 324:776–777 (1991) and Rumsfield et al. (1991) Annals Pharmacother 25 381–387. Little is known about the extent of topical absorption of compounds through intact skin. It is known, however, that drugs will not penetrate into deeper tissues after topical application if the stratum corneum barrier is not overcome. Complete removal of this barrier should yield tissue levels equivalent to those observed after dermal application. Iontophoresis (movement of solutes into the skin using an electrical potential difference) also yields tissue concentrations for lignocaine and salicylic acid in vivo which are similar to those observed after dermal application as discussed in Singh et al. (1993) J Pharm Sci 82 127–131. Transport of solutes such as vasodilators or any other active agent(s) by iontophoresis is not a straightforward process with many of the factors controlling penetration through epidermis still under investigation. It is only in the last few years that the permselectivity and pore properties of the skin (Burnette et al. J Pharm Sci 77 132–137 in 1988) and voltage drop across the skin (Masada et al. Int. J Pharm 49 567–62 1989) have been characterised (see Singh et al. Drug Design and Delivery 4 1–12 in 1989). Much of the early work was based on clinical observation. Aspirin iontophoresis, introduced for the management of rheumatic diseases in 1903, continues to be used successfully for this purpose as discussed in Garagiola et al. Clin Ther 10 553–558 in 1988.

Reference may be made to Japanese Patent Specification JP 04300833 which describes topical sprays useful for the treatment of burns, skin ulcers, decubitus and alopecia which contain the vasodilator eicosanoid prostaglandin $E_1$ ($PGE_1$), together with a suitable vehicle which comprises fat emulsions, purified egg yolk, lecithin, oleic acid, purified soybean oil and glycerine.

Japanese Patent Specification JP 03083925 describes the use of prostaglandin $PGE_1$ in combination with saturated fatty alcohols, glycols and organic acids as stabilizers or absorption promoters. These compositions were useful for treatment of Raynaud's disease, decubitus, dermal ulcers, psoriasis, arteriosclerosis and also as compositions for promoting hair growth.

Patent Specification JP 03011017 describes the use of $PGE_1$ containing collagen sheets for topical application such as treatment of burns and wounds. The collagen sheets also included soyabean oil, lecitin, sodium oleate and phosphatidic acid which were useful as vehicles for the $PGE_1$ for absorption into the collagen sheets.

Prostaglandin $I_2$ ($PGI_2$) has also been described in topical ointments having been shown to be effective in the treatment of skin ulcers in patent specification JP 04243827. Other components of the topical ointment included fatty acid esters as solubilizers and paraffins as vehicles or bases. Specification JP 04164034 also describes $PGI_2$ which is included in a topical preparation which also contains water soluble cellulose and lower alkyl ethers for use in relation to treatment of skin ulcers.

The calcium channel antagonists nifedipine and verapamil which are also examples of vasodilator compounds suitable for topical application have previously been described for use in the inhibition of cutaneous, ocular or mucosal hypersensitivity reactions, inflammation, hyperproliferation or scarring, as stated in patent specification ZA 90-6583 and for treating hypertrophic scar formation, as stated in patent specification WO 9101624.

Reference may also be made here to European Specifications 449463 and 448299 which discloses methods and compositions for enhanced blood removal of iontophoretically delivered active agents in combination with a vasodilator and vasoconstrictor respectively. During iontophoresis charged compounds pass from a reservoir attached to the skin of a person into the tissue underneath. The process is one wherein the rate of delivery is a function of current, active agent concentration and presence of other ions. Generally, iontophoretic devices comprise at least two electrodes, an electrical energy source, such as a battery and at least one reservoir which contains an active agent to be delivered. It is hypothesized in these specifications that local vasodilation or local vasoconstriction will increase the rate of active agent absorption, and aid its distribution to reach peak concentrations in the systemic vasculature.

European Patent 449463 refers specifically to a composition for iontophoretic delivery comprising a delivery enhancing amount of a vasodilator and active agent. European Patent 448299 refers specifically to a composition for iontophoretic delivery comprising a delivery enhancing amount of a vasoconstrictor and active agent.

In specific regard to European Patents 449463 and 448299 where ionised and polar solutes are used it will be appreciated that such compositions could not be applied to intact skin whereby solutes should be un-ionised and lipid soluble.

With regard to the state of the art concerning the application of active agents to wound or damaged tissue sites, reference can be made to patent specification WO 8900848 which describes the application of an oxygenated fluid (particularly perfluorohydrocarbons) to damaged tissue, thereby making oxygen available to the tissue, optionally with the inclusion of other therapeutic agents mixed into the fluid. Wound dressings containing active agents have also been described in specification EP 88-402820. However, this specification deals specifically with a wound dressing including a substrate and a physiologically or biologically active agent absorbed therein. The substrate is chemically modified to have ionic-absorbing sites thereon and the agent is in its ionic form. Upon contact with body exudate from wounds, the active agent is released in a controlled manner by ion exchange with the ions in the body exudate, in proportion with the amount of exudate.

Reference may also be made to patent specification JP 8747592 which describes a pharmaceutical composition for application to a wound site such as bed sores comprising a mixture of sugars, potassium, disinfectants, antibiotics or antimicrobial agents, inflammation inhibitors, vitamins, proteases, protease inhibitors, transudate absorbents, keratin dissolvers, vasodilators and bases. However, the vasodilator which is utilised in this reference in a wound fluid is clearly one that would not be suitable for topical application.

In regard generally to the state of the art concerning use of vaso-active agents in combination with therapeutic agents, the only technique reported [i.e. in Ledger, Advanced Drug Delivery Reviews 9 289–307 (1992)] that may be utilised for application of vaso-active agents to locations under the stratum corneum such as the dermis, subcutaneous, fascia, smooth muscle, muscle fat pad, deep muscle and plasma is iontophoresis. However, it will be appreciated that iontophoresis has the following disadvantages:

(i) this technique normally can only be utilised for relatively short time intervals, i.e. of the order of 30 minutes;

(ii) use of this technique may cause increased blood flow, pain, irritation, dermatitis and, in some instances, burns, which are undesirable;

(iii) this technique is not normally utilised in difficult or inaccessible locations such as between the toes, under the arms, or on the nose.

BROAD STATEMENT OF INVENTION

Figure 1:
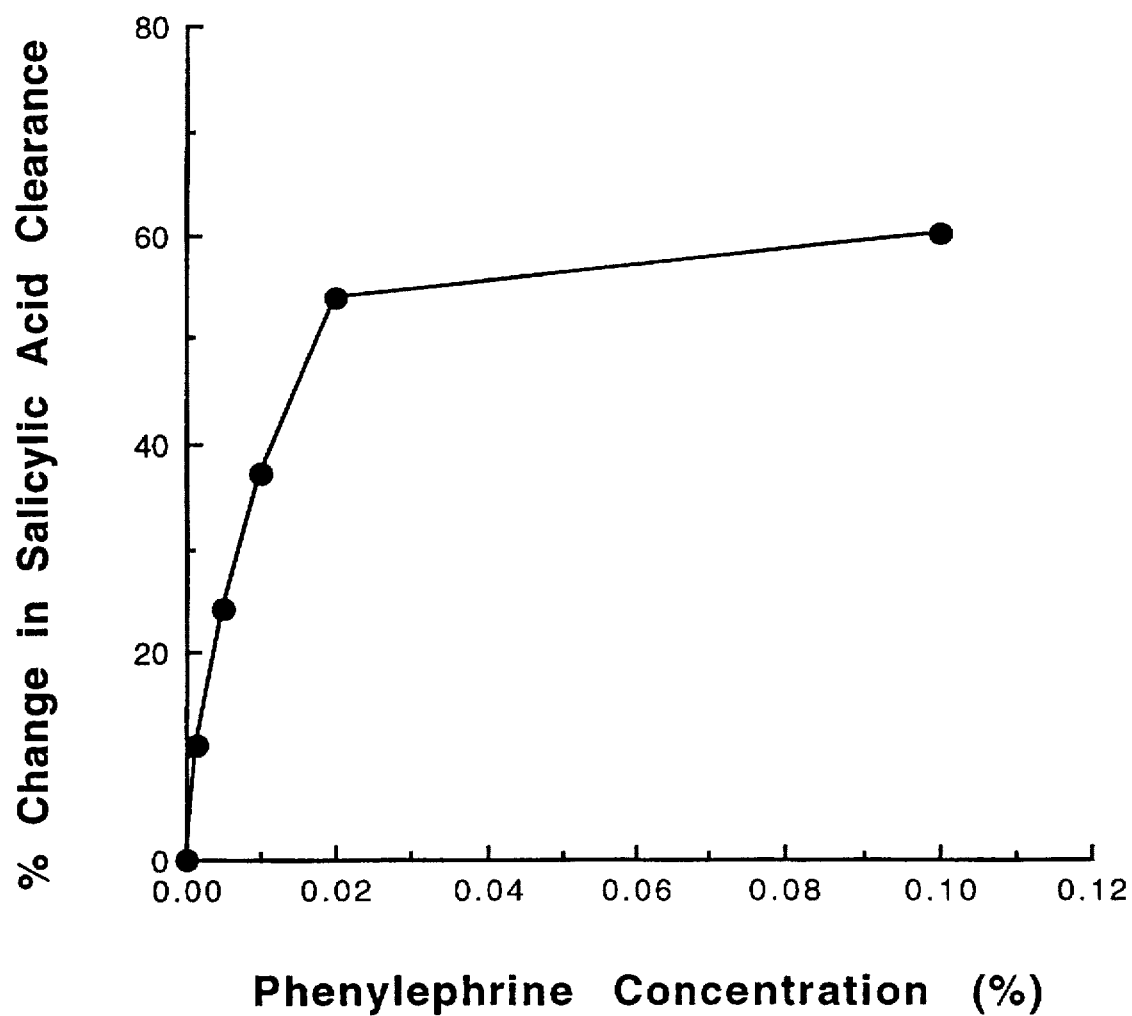
FIG. 1 shows the relationship between the phenylephrine concentration and the dermal clearance of salicylic acid after application to rat dermis.

It is therefore an object of the invention to provide a method of topical and/or transdermal administration of a vaso-active agent in combination with a therapeutic agent selected from an anti-inflammatory agent or anaesthetic to modify local perfusion and/or concentration of the therapeutic agent in body fluid such as serum in tissues adjacent the administration site of the vaso-active agent.

It is also an object of the invention to provide a composition of both vaso-active agent and therapeutic agent which will be useful in the method.

The method of the invention therefore in one aspect includes the steps of:

(i) determination of a concentration of vaso-active agent which is appropriate for a targeted location under the stratum corneum which is selected from the dermis, subcutaneous, fascia, smooth muscle, muscle, fat pad, deep muscle and plasma which concentration corresponds to the degree of penetration of the therapeutic agent to said targeted location relative to an initial concentration of therapeutic agent which is applied topically or locally; and (ii) administration of the vaso-active agent using at least the concentration determined in step (i) in combination with the therapeutic agent at said initial concentration or wherein the vaso-active agent using at least the concentration determined in step (i) is administered separately to the therapeutic agent which is utilised at said initial concentration.

As will be apparent hereinafter, the first aspect of the invention is illustrated in FIG. 2 with salicylate being a suitable therapeutic agent and the vaso-active agent being phenylephrine.

However, in accordance with a second aspect of the present invention, step (ii) may be applied to administration of a second or different vaso-active agent to that of a first vaso-active agent utilised in step (i). In the second aspect of the invention, the concentration of the second vaso-active agent may be calculated from the equation $$\text{CONCENTRATION OF SECOND VASO-ACTIVE AGENT} = \frac{\text{EQUIVALENT CONCENTRATION OF FIRST VASO-ACTIVE AGENT} \times \frac{\text{POTENCY OF SECOND VASO-ACTIVE AGENT}}{\text{POTENCY OF FIRST VASO-ACTIVE AGENT}}}{}$$

A "vaso-active agent" in accordance with the invention may include within its scope any substance that alters blood vessels which in turn may alter blood flow through those vessels. The vaso-active agent therefore includes vasodilators, vasoconstrictors, a precursor of a vasodilator or vasoconstrictor such as arachidonic acid.

The therapeutic agent(s) as described above are useful in treatment or having a therapeutic effect on tissues below the stratum corneum and thus cannot include substances which are primarily vehicles or carriers or solvents for a particular therapeutic agent or topical treatment agents which are intended for application only to the stratum corneum.

As stated above, the therapeutic agent may be administered separately to the administration of the vaso-active agent and this may be achieved by administration of the therapeutic agent (i) at an adjacent site to the site of administration of the vaso-active agent, (ii) at the same or adjacent site to the site of administration of the vaso-active agent separated by a relatively short time interval, or (iii) by a different route (e.g. systemically) when compared to the topical administration of the vaso-active agent.

Compositions comprising the vaso-active agent and therapeutic agent will be found in accordance with this invention as having excellent skin penetration and therefore may be used in transdermal therapeutic systems as a drug reservoir, or applied topically to the skin, epidermis, dermis, subcutaneous tissue, fascia, muscle, fat, joints or bones, wounds, blister and ulcer beds, granulating tissue, newly formed epithelium, scar tissue and any other lesioned or abnormal site contained between the depth of skin to muscle.

When vasodilators are used in regard to the composition of the invention they are useful in facilitating local blood flow adjacent a particular tissue site thereby facilitating not only faster delivery of the therapeutic agent but also in higher concentrations. Vasodilators may also facilitate removal of therapeutic substances from a particular site compared to the situation when vasodilators are not used and it will also be appreciated that vasodilators may facilitate deeper penetration into the tissue by therapeutic agent(s) via the local arrangement of blood vessels.

Vasoconstrictors when used in the composition of the invention may also facilitate an increased concentration of therapeutic agent(s) adjacent the site of administration when compared to the situation when a vasoconstrictor is not used and may also increase the depth of tissue penetration of the therapeutic agent(s) by decreasing the rate at which the therapeutic agent(s) is cleared by the local blood supply.

In the composition of the invention the therapeutic agent (s) ay be present in pharmaceutically acceptable chemical combination with the vaso-active agent. The composition may also include a suitable vehicle or carrier for both therapeutic agent and vaso-active agent. In the case of a therapeutic agent, a suitable vehicle may comprise an appropriate excipient for percutaneous delivery.

Examples of anti-inflammatory agents useful as therapeutic agents that may be used in the method of the invention include non-steroidal anti-inflammatory agents (NSAIDS) which if taken orally may cause irritation of the stomach or intestine. Oral administration of NSAIDS may also cause dyspepsia. However, in accordance with this invention if the NSAIDS are applied topically such as in combination with a cream, gel, spray, patches or other form of transdermal treatment system (TTS) these disadvantages may no longer apply.

Examples of other anti-inflammatory agents that may be used in the method of the invention include antipruritics, steroidal anti-inflammatory agents inclusive of corticosteroids, antihistamines, endogenous cellular mediators or their stable analogues and analgesics.

Specific examples of suitable corticosteroids include hydrocortisone and descamethasone. Examples of arthritics include indomethacin and diclofenac. Antipruritics include cyclodine hydrochloride and benzocaine. Local anaesthetics suitable for use include lidocaine, ropivicaine and mepivicaine. Salicylates may also be used.

The therapeutic agent included in the composition of the invention may also be a prodrug or precursor.

The therapeutic agent may also comprise an unionised compound which may be solid or in solution with the latter being the more usual situation. The therapeutic compound may also comprise an ion pair such as an NSAID which are all anions in the ionised state in combination with a vasoconstrictor which are all cations in solution. One could also use a neutral compound such as a salt comprising the anion of a fatty acid in combination with a protonated amine such as R—COO⁻ NH₃⁺. An example of such an ion pair is salicylate prior in combination with amine cations inclusive of ethylamine, diethylamine, triethylamine, triethanolamine, pentylamine and dodecylamine.

Therefore in this aspect of the invention the vasodilator and/or vasoconstrictor can be combined with the active compound e.g. in the form THERAPEUTIC COMPOUND⁻ VASO⁺.

The method of administration of the compound is suitably with all components in admixture and applied directly to the skin or by way of transdermal treatment systems as described above or alternatively the components may be administered individually and separated by a short time interval e.g. of the order 15–60 min more preferably 30 min.

In all of the above examples the therapeutic agent is neutral and lipophilic in its complexed or natural forms.

It will also be appreciated that the term "topical" as used herein covers administration to the mouth, penis, nose, eye, ear, vagina, anus or any other body part accessible to local administration such as the lungs being accessible to an aerosol administration of the composition of the invention.

Vasoconstrictors for use in the compositions of the invention may include any chemical entity which is suitable for topical delivery that is capable of decreasing blood flow by constriction of any elements of the vasculature or that effect constriction via numeral mechanisms supplying the vasculature. In other words the use of vasoconstrictors in the composition of the invention is able to increase the rate and depth of tissue penetration at the site of application by decreasing the rate at which it is cleared by the local blood supply. Examples of suitable vasoconstrictors include alphaadrenergic agonists which may include adrafinil, adrenaline, amidephrine, apraclonidine, budralazine, clonidine, cyclopentamine, detomidine, dimetofrine, dipivefrin, ephedrine, epinephrine, fenoxazoline, guanabenz, guanfacine, hydroxyamphetamine, ibopamine, indanazoline, isometheptene, mephentarmine, metaraminol, methoxamine hydrochloride, methylhexaneamine, metizoline, midodrine, naphazoline, norepinephrine, norfenefrine, octodrine, octapamine, oxymetazoline, phenylephrine hydrochloride, phanylpropanolamins hydrochloride, phenylpropylemethylamine, pholedrine, propylhexedrine, pseudoephedrine, rimenidine, synephrine, tetrahydrozoline, tiamenidine, tramazoline, tuaminopheptane, tymazoline, tyramine and xylometazoline. Other vasoconstrictors include epinephrine, noradrenaline, ephedrine, as well as imidazolines which may include naphazoline (2-(1 naphthyimethyl) imidazoline), oxymetazoline (2-(4-tert-butyl-2,6-dimethyl-3-hydroxbenzyl)-2-imidazoline), tetrahydrozaline (2-(1,2,3,4-tetrahydro-1-naphthyl)-2-imidazoline)), fenoxazoline (2-[(0-cumenyloxy)methyl]-2-imidazoline), indanazoline (N-(2-imidazolin-2-yl)-N-(4-indayl)amine), tramazoline (2-[(5, 6,7,8 tetrahydro-1-naphthyl)amino] -2-imidazoline, tymazoline (2-[(thymyloxy)-methyl]-2-imidazoline), and xylometazoline (2-(4-tert-butyl-2, 6-dimethylbenzyl)-2-imidazoline).

Vasodilators for use in the composition of the invention include any chemical entity, which is suitable for topical delivery, that is capable of increasing blood flow by dilatation of any elements of the vasculature or that effect dilatation via neuronal mechanisms supplying the vasculature or that effect dilatation via the release of endogenous mediators which then have an effect on the vasculature or elements of neuronal mechanisms of the vasculature. The use of vasodilators in the composition of the invention is able to increase the rate of systemic absorption of the active compound of interest by enhancing the rate at which it is cleaned from the application site by the local blood supply.

Examples of suitable vasodilators include lidocaine, nitroglycerine and other organic nitrates, or glyceryl trinitrate, papaverine, nicotinates and various prostaglandins (more correctly eicosanoids) and various calcium antagonists.

Vehicles or excipients which may be used in the composition of the invention include any non toxic non aqueous compound such as an oil such as paraffin which are suitable for topical application and which are liquid at room temperature. Paraffins may comprise purified clear, oily, tasteless and odourless mixtures of saturated aliphatic or cycloaliphatic hydrocarbons e.g. low viscosity or viscous paraffin such as sold under the Registered Trade Mark VASELINE. Other preferred excipients for percutaneous delivery include those which are suitable for the preparation of creams, liniments, ointments, aerosol sprays, gels, pastes or foams suitably containing 0.5 to 5.0% of vaso-active agent in aqueous phase of viable epidermis.

The compositions of the invention may be applied directly to the skin or by the use of transdermal treatment systems (TTS) which may include (a) patches which are semi permeable membranes with the active compound applied to a top surface thereof; (b) an active compound dissolved in a plastics compound such as polyethylene or polyvinyl chloride; (c) an active compound printed on a top surface of a plastics compound e.g. by laser. Other examples of TTS include (i) to (iv) referred to above in regard to U.K. Patent 2 192 539.

It will be found in practice that the compositions of the invention may be used to target any tissue area included in the epidermis, dermis, subcutaneous tissue, fascia, muscle, fat pad, deep muscle, joints or bones. The administration of a therapeutic compound in accordance with the invention travels to the site requiring attention more quickly than by oral administration and thus the compositions of the invention may be used in relation to treatment of arthritis, sciatica and rheumatism. Another advantage of administration of the composition of the invention is essentially a localised application which will alleviate chronic pain.

While it is preferred that the vaso-active agent be administered prior to administration of the therapeutic agent it will be appreciated that the therapeutic agent can be administered prior to the vaso-active agent if necessary.

Concentrations of therapeutic agent are up to the saturation solubility of the respective agents in general. It is possible that supersaturated solutions and suspensions of the agents may also be used. Experimental data to date suggest that there is an optimal range of concentrations that exist for any given vasodilator or vasoconstrictor wherein the desired local effects and achieved without significant effects on the rest of the body. For example, in FIG. 3 it is observed that in the deep muscle at a phenylephrine concentration in the epidermis at 0.01% maximum concentrations of salicylic acid and observed in this tissue. At higher concentrations this fraction decreases and is consistent with changes in the plasma concentration and systemic effects.

The concentration of the vasoconstrictor for use in the composition of the invention may be determined by reference to FIG. 2 hereinafter and from the equation.

$$\text{CONCENTRATION OF VASOCONSTRICTOR} = \frac{\text{EQUIVALENT CONCENTRATION OF PHENYLEPHRINE}}{\text{POTENCY OF PHENYLEPHRINE}} \times \text{POTENCY OF VASOCONSTRICTOR}$$

The concentration of the vasodilator may be determined by a similar equation whereby a series of graphs similar to FIG. 2 are constructed with reference to a particular vasodilator. In our experience high concentrations of vasodilators lead to systemic vasodilation which will limit the depth of penetration.

These concentrations are those required below the stratum corneum. Adjustment for the vaso-active agent in the vehicle and the permeability coefficient of the vaso-active agent through the skin allows this invention to be applied to topical vehicles more generally. Thus, in other words, the concentration of vaso-active agent in the topical vehicle may be calculated from the above data.

Reference is made to a text book on general pharmacology e.g. Goodman & Gilman entitled "The Pharmacological Basis of Therapeutics" (published by Pergamon Press) for potency values of particular vasoconstrictors and vasodilators.

Generally the maximum concentration of ephedrine which is a vasoconstrictor has a water solubility of 50 mg/ml ag/cm and gives a maximum flux through skin of 250–400 $\mu g/cm^2$ per hr at 30° C. as discussed in Michaels et al. AiChE Journal 21 (1975) pp 985.

The vasodilator nitroglycerine has a water solubility of 1.3 mg/ml and gives a maximum flux of 10–25 $mg/cm^2/hr$ through human skin.

The foregoing information on ephedrine will apply also to other parameters that are applicable to any other vasoconstrictor and a similar conclusion apply to any other vasodilator having regard to the information above on nitroglycerine.

EXAMPLE 1

Chemicals and Instruments: [$^{14}$C]Salicylic acid (specific activity 56 mCi/mmol, purity>98.0%) was a gift from Hamilton Labs (Australia) Pty Ltd, [$^{14}$C]lidocaine hydrochloride (specific activity 48 mCi/mmol, purity>97.0%) and tritiated water (1 mCi/g) were purchased from New England Nuclear, USA. Salicylic acid and phenylephrine hydrochloride were from Sigma Chemical Company, USA, and lidocaine hydrochloride was a gift from Astra Pharmaceuticals (Australia) Pty. Ltd. Zimmer's electrodermatome (Model 901, USA) was used for removing rat epidermis. Tissue solubiliser, NCS, and liquid scintillation cocktails OCS (organic counting scintillant) and BCS (Biodegradable counting scintillant) for tissue and aqueous samples respectively were purchased from Amersham International, England. All other reagents used were of analytical grade. A liquid scintillation counter (Tri-carb®4000 series, United Technologies Packard, USA), was used to determine the radioactivity in the samples. Animals: Male Wistar rats (300–350 G) were used in the studies. The animals were housed under standard laboratory conditions 20.0°±0.5° C., relative humidity 55–75% and supplied with normal pellet diet and water ad libitium. All experiments had previously been approved by the Animal Experimentation Committees of the University of Queensland and the Princess Alexandra Hospital.

In vivo dermal penetration and local tissue uptake studies: The rats were lightly anaesthetised by pentobarbitone (35 mg/kg) and their body temperature maintained at 37° C. by placing them on a heating pad. The hair from the 4 $cm^2$ dorsum area were removed by electric clippers and the epidermis removed by means of an electrodermatome set at a thickness of 80 microns. A dermal absorption cell was adhered to the exposed rat dermis and warmed to 37° C. by means of an external heating device.

Solution of solute spiked with corresponding labelled substance and containing an appropriate concentration of phenylephrine, previously warmed to 37° C., was introduced into the dermal absorption cell and the solution stirred by a glass stirrer driven by an external motor. Samples were removed from the donor cell at predetermined times and placed in preweighed scintillation vials. The glass cell was removed from the rat skin at the end of two hour dermal perfusion study and the application area wiped dry with blotting paper. A blood sample was then taken from the tail vein and the animals sacrificed with overdoes of anaesthetic ether. Immediately thereafter the tissues below the treated site i.e. skin, subcutaneous tissue, fascia, muscle lining or superficial muscle, muscle, fat pad and deep muscle were removed from dissection and placed in preweighed scintillation vials. Similarly, the tissues below the contralateral side were also removed. Tissue and plasma samples were stored at −20° C. prior to analysis. In vivo dermal penetration and local tissue uptake studies (sacrificed animals): The rats were initially anaesthetised by intraperitoneal injection of pentobarbitone (35 mg/kg) and after removing epidermis as described above, were sacrificed by overdose of ether. Dermal perfusion and tissue uptake studies were then conducted in postmortem rats.

Blood Flow measurements

The blood flows to different tissues estimated in our earlier study were used. The dermal clearance of tritiated water has been shown to closely reflect the blood flow to dermis. The phenylephrine induced reduction in blood flow to dermis was determined by monitoring the dermal clearance of tritiated water in presence of phenylephrine.

Sample treatment

Aqueous samples removed from the glass cells in in vivo dermal perfusion studies were directly mixed with 5 ml of liquid scintillation cocktail BCS and counted on liquid scintillation counter. The tissue samples were solubilised with 50 $\mu$l of water and 1 ml of tissue solubilizer NCS at 50° C. for 6–8 hrs. After cooling the digested samples to room temperature, 0.03 % of glacial acetic acid was added to each tissue sample followed by 10 ml of organic scintillant OCS. The plasma samples were solubilised with tissue solubilizer (5 parts for one part of plasma) at room temperature and treated with glacial acetic acid before adding OCS. Each sample was then counted on the liquid scintillation counter for 10 minutes.

FIG. 1 shows the dependence of changes in salicylic acid clearance from solutions applied to the dermis with increasing concentrations of phenylephrine. The clearance decreased up to phenylephrine concentration of 0.05%. At higher phenylephrine concentration (0.1%) no further decrease in salicylic acid clearance is apparent. Phenylephrine constricts dermal blood vessels and lowers the local blood flow in the dermal tissue, thereby reducing the clearance of salicylic acid. The clearance of lidocaine, and tritiated water showed a similar decrease for the two concentrations of phenylephrine studied (1:20,000 and 1:5,000) (Table 1) relative to control solutions. The disappearance of methotrexate, steroids and local anesthetics has also been shown to be reduced from dermal and subcutaneous sites under postmortem conditions which represents an extreme case of vasoconstriction.

Figure 2A:
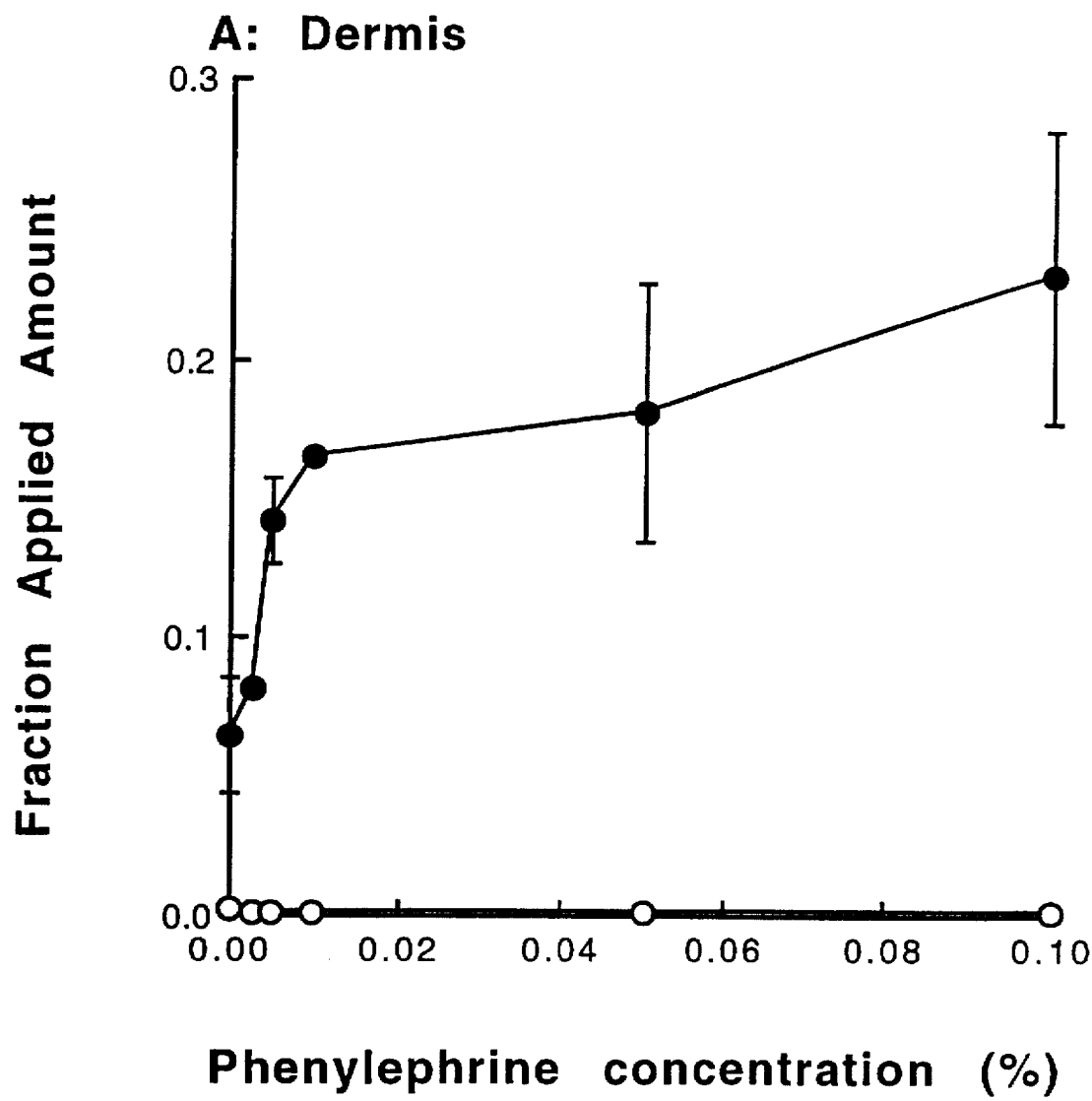
FIG. 2a shows the relationship between the phenylephrine concentration and the concentration of salicylic acid (expressed as a fraction of initial donor concentration) in underlying tissues (●) and contralateral tissues (○) below the skin (dermis) after dermal application.
Figure 2B:
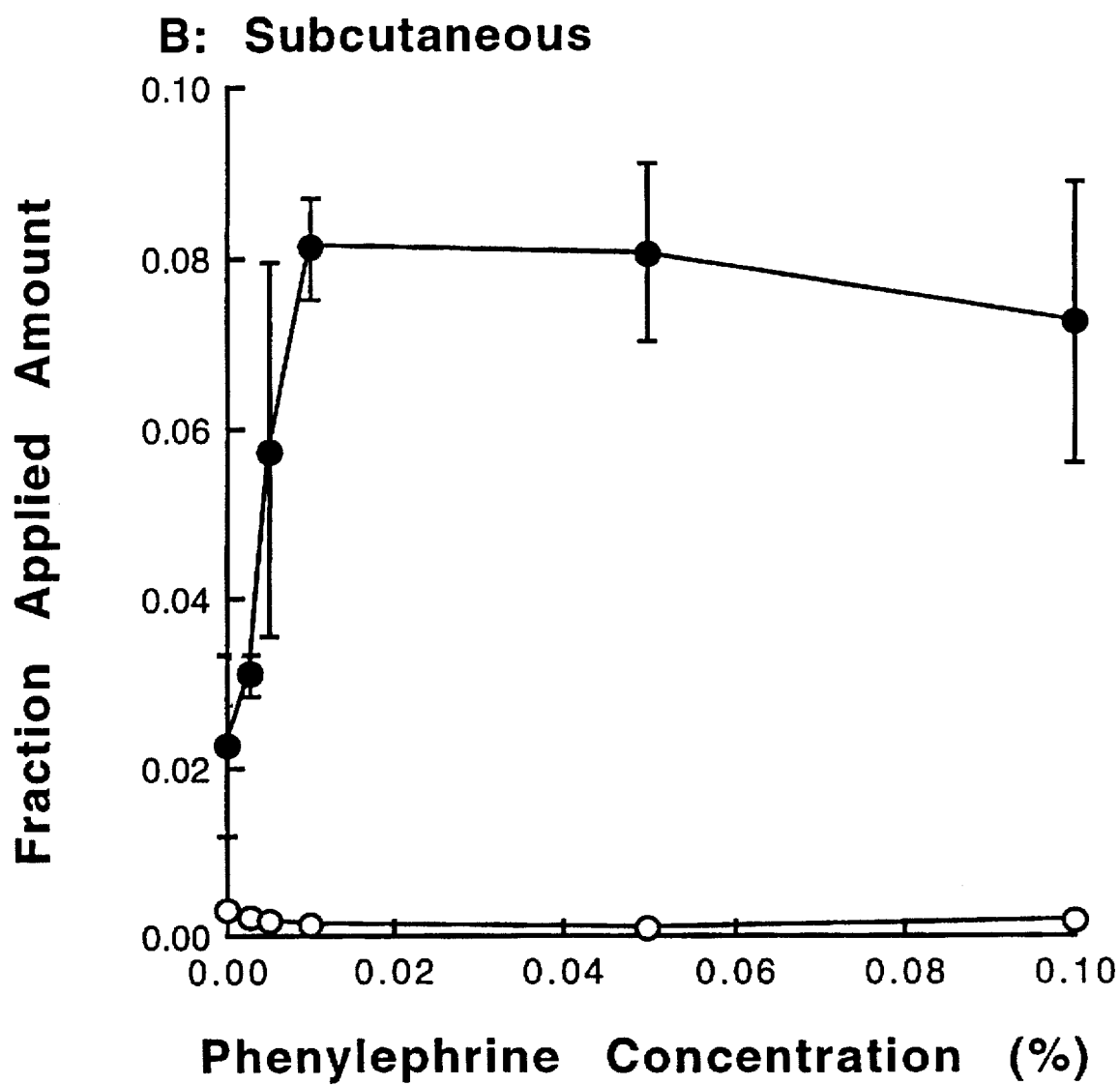
FIG. 2b shows the relationship between the phenylephrine concentration and the concentration of salicylic acid (expressed as a fraction of initial donor concentration) in underlying tissues (●) and contralateral tissues (○) below the subcutaneous tissue after dermal application.
Figure 2C:
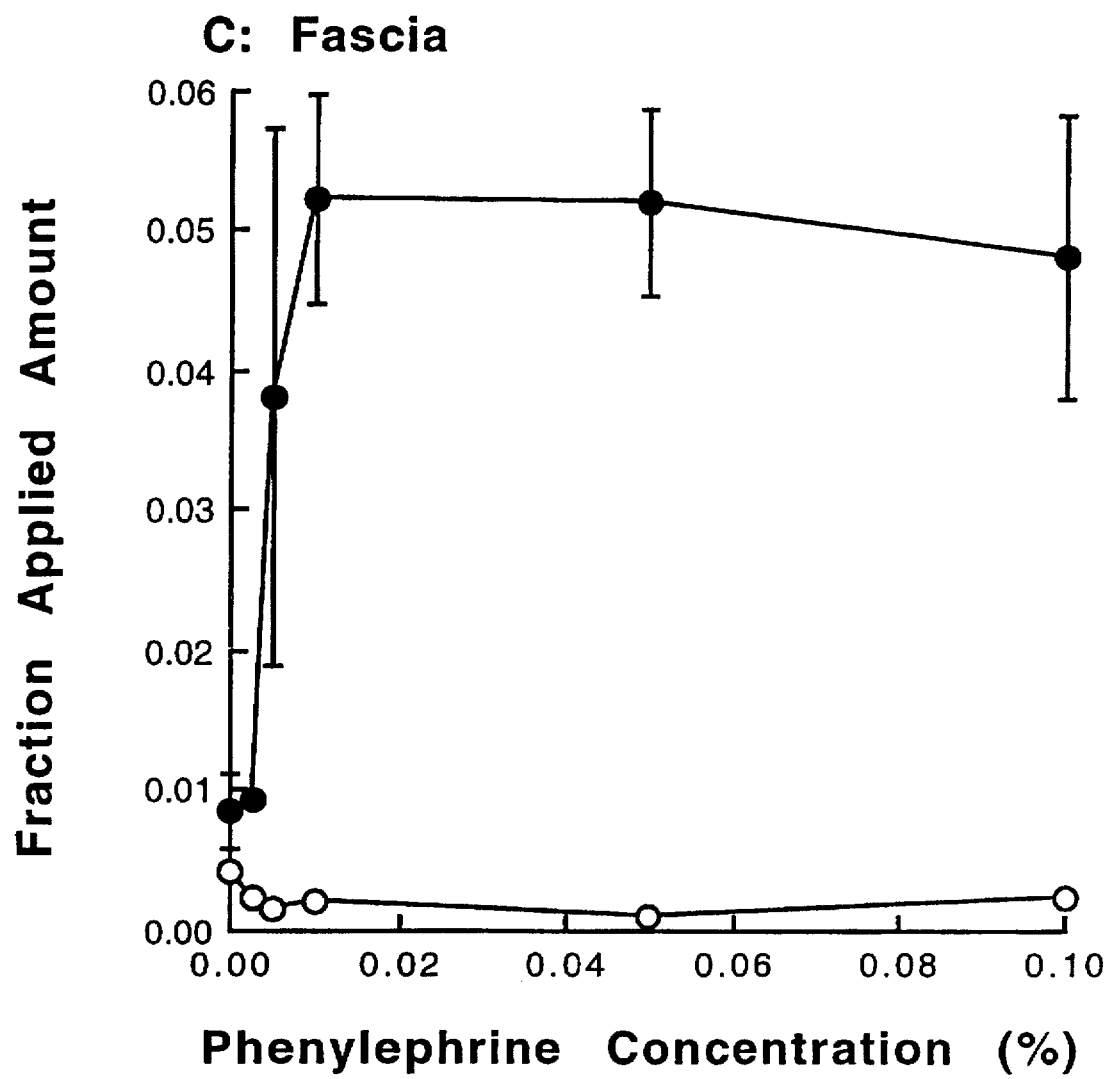
FIG. 2c shows the relationship between the phenylephrine concentration and the concentration of salicylic acid (expressed as a fraction of initial donor concentration) in underlying tissues (●) and contralateral tissues (○) below the fascia after dermal application.
Figure 2D:
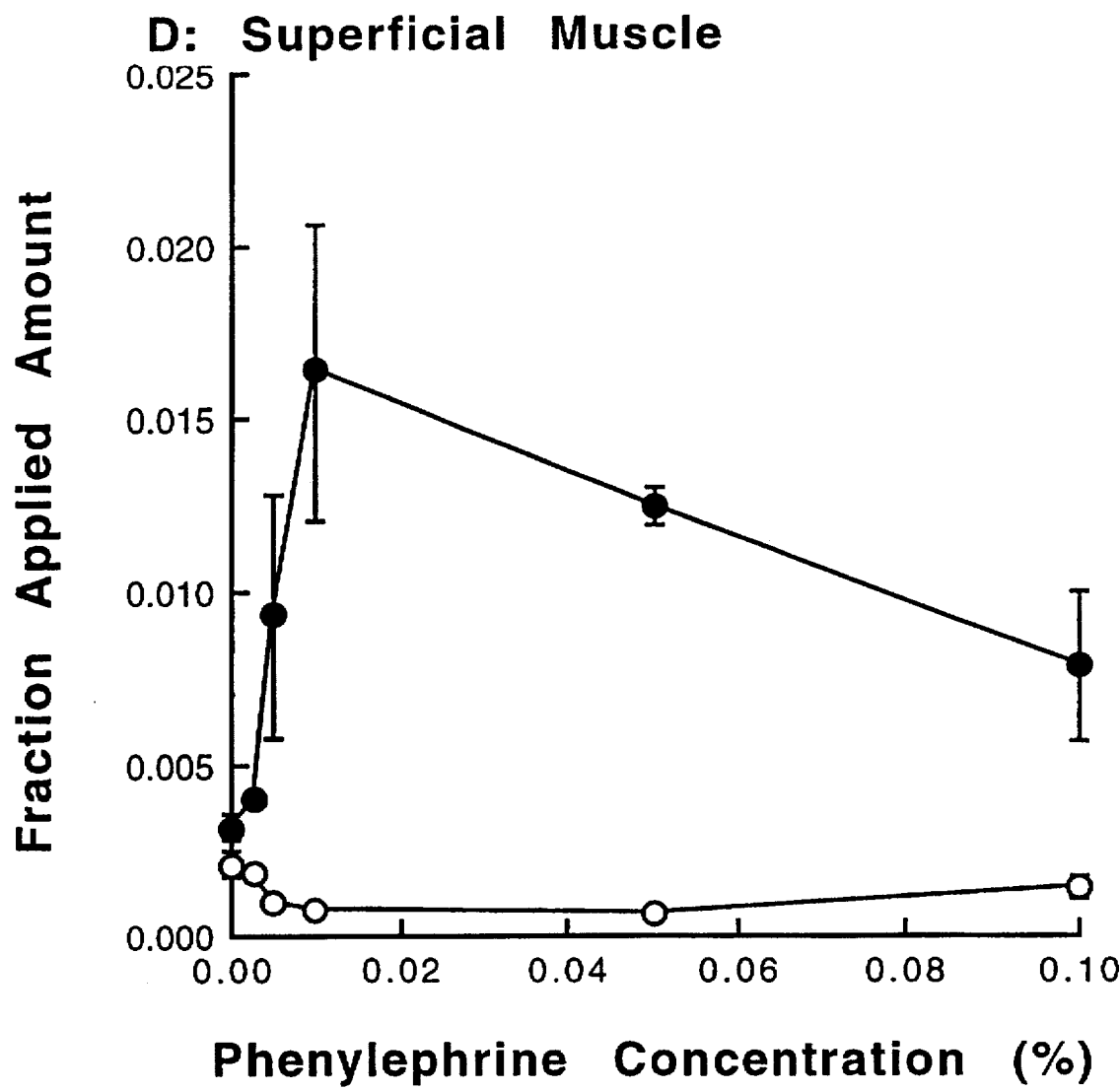
FIG. 2d shows the relationship between the phenylephrine concentration and the concentration of salicylic acid (expressed as a fraction of initial donor concentration) in underlying tissues (●) and contralateral tissues (○) below the superficial muscle after dermal application.
Figure 2E:
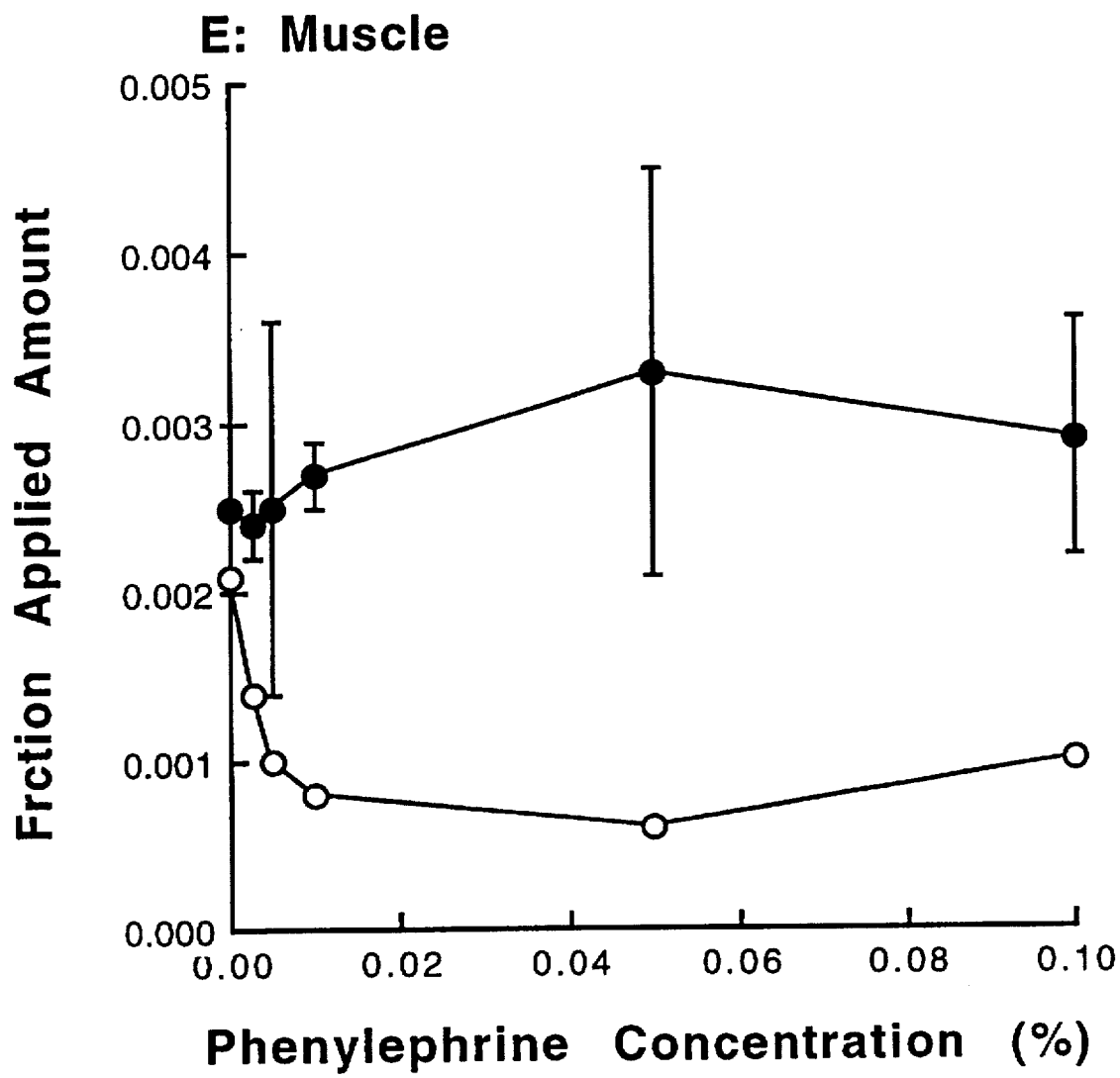
FIG. 2e shows the relationship between the phenylephrine concentration and the concentration of salicylic acid (expressed as a fraction of initial donor concentration) in underlying tissues (●) and contralateral tissues (○) below the muscle after dermal application.
Figure 2F:
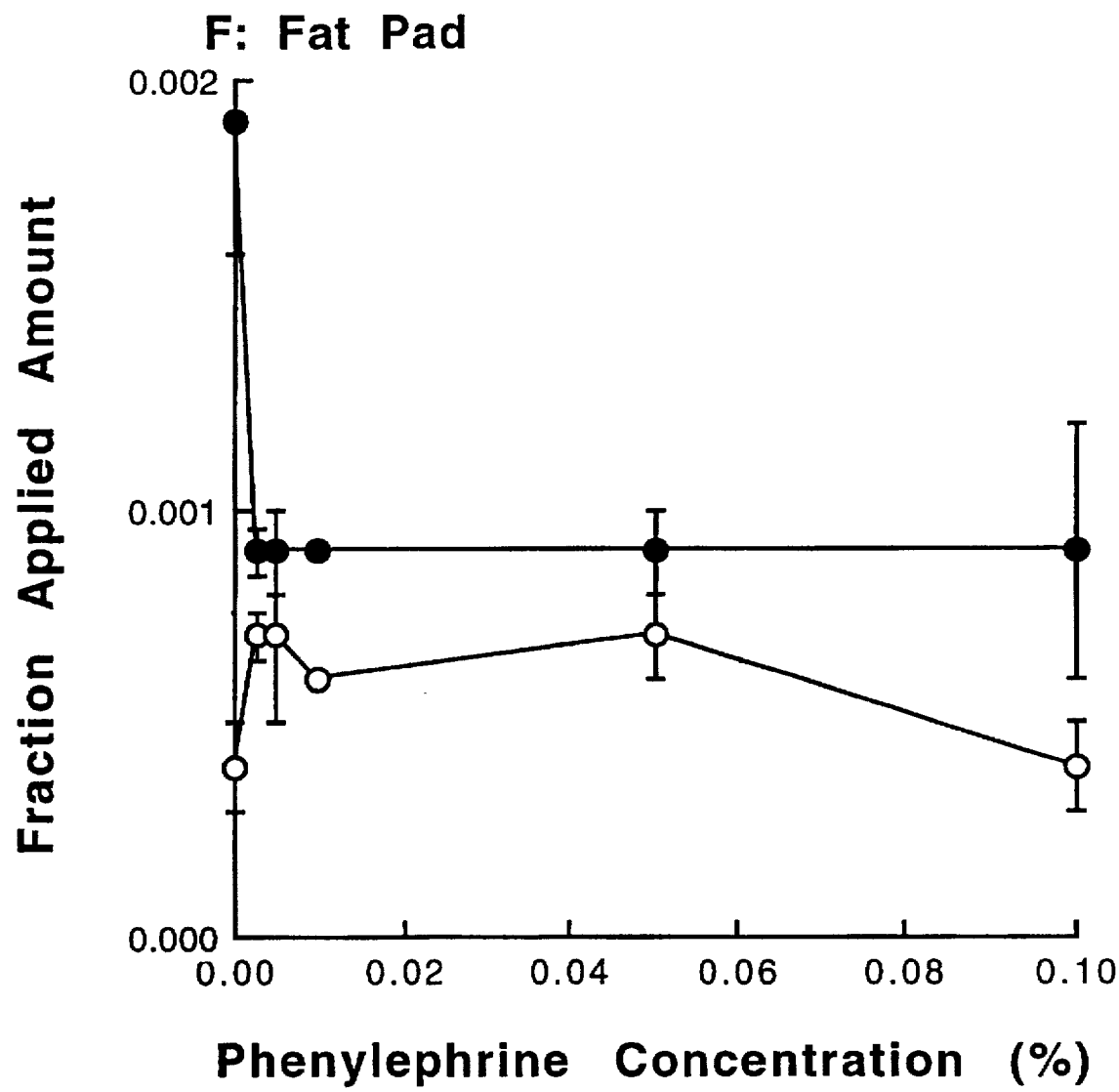
FIG. 2f shows the relationship between the phenylephrine concentration and the concentration of salicylic acid (expressed as a fraction of initial donor concentration) in underlying tissues (●) and contralateral tissues (○) below the fat pad after dermal application.
Figure 2G:
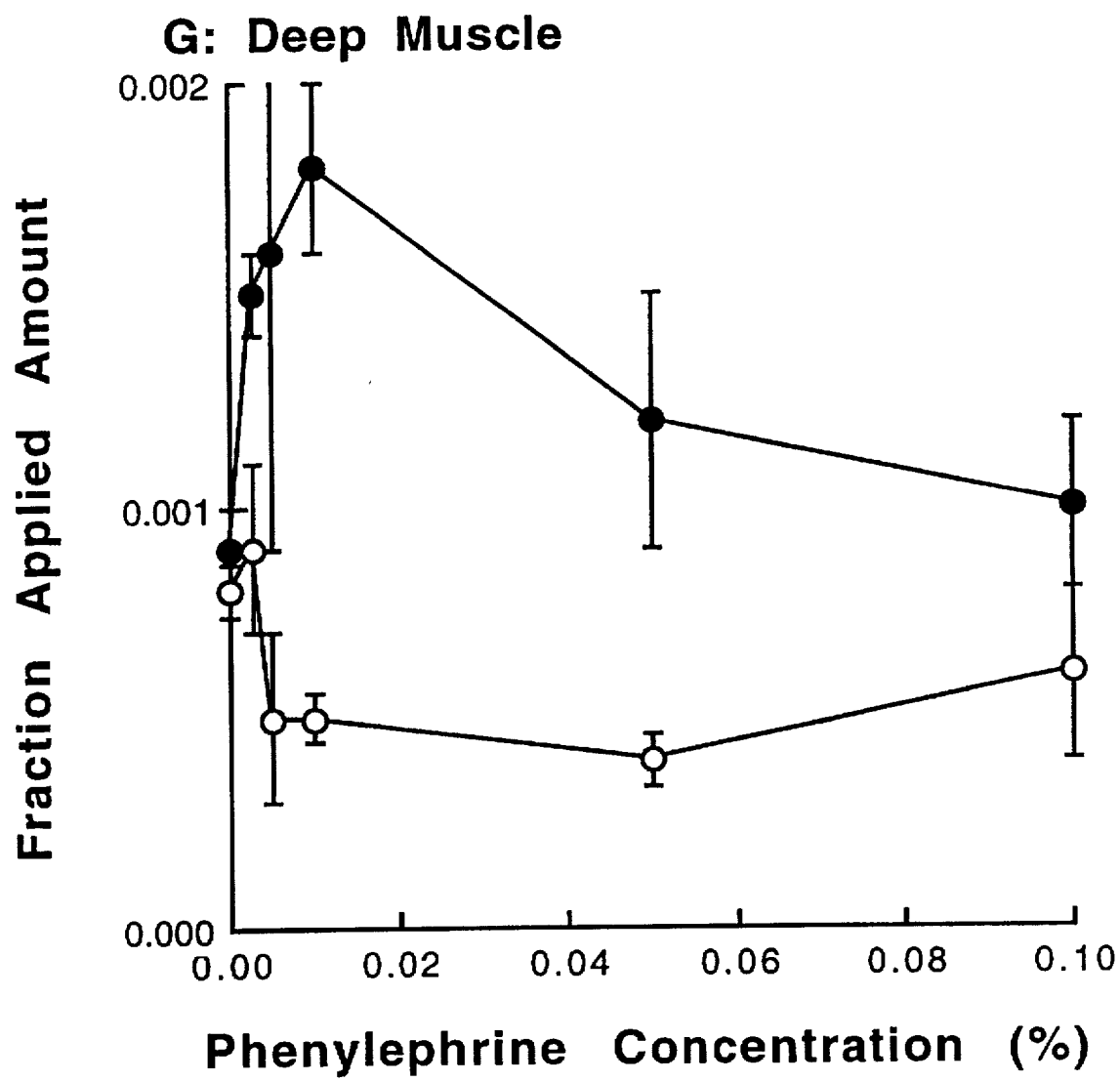
FIG. 2g shows the relationship between the phenylephrine concentration and the concentration of salicylic acid (expressed as a fraction of initial donor concentration) in underlying tissues (●) and contralateral tissues (○) below the deep muscle after dermal application.
Figure 2H:
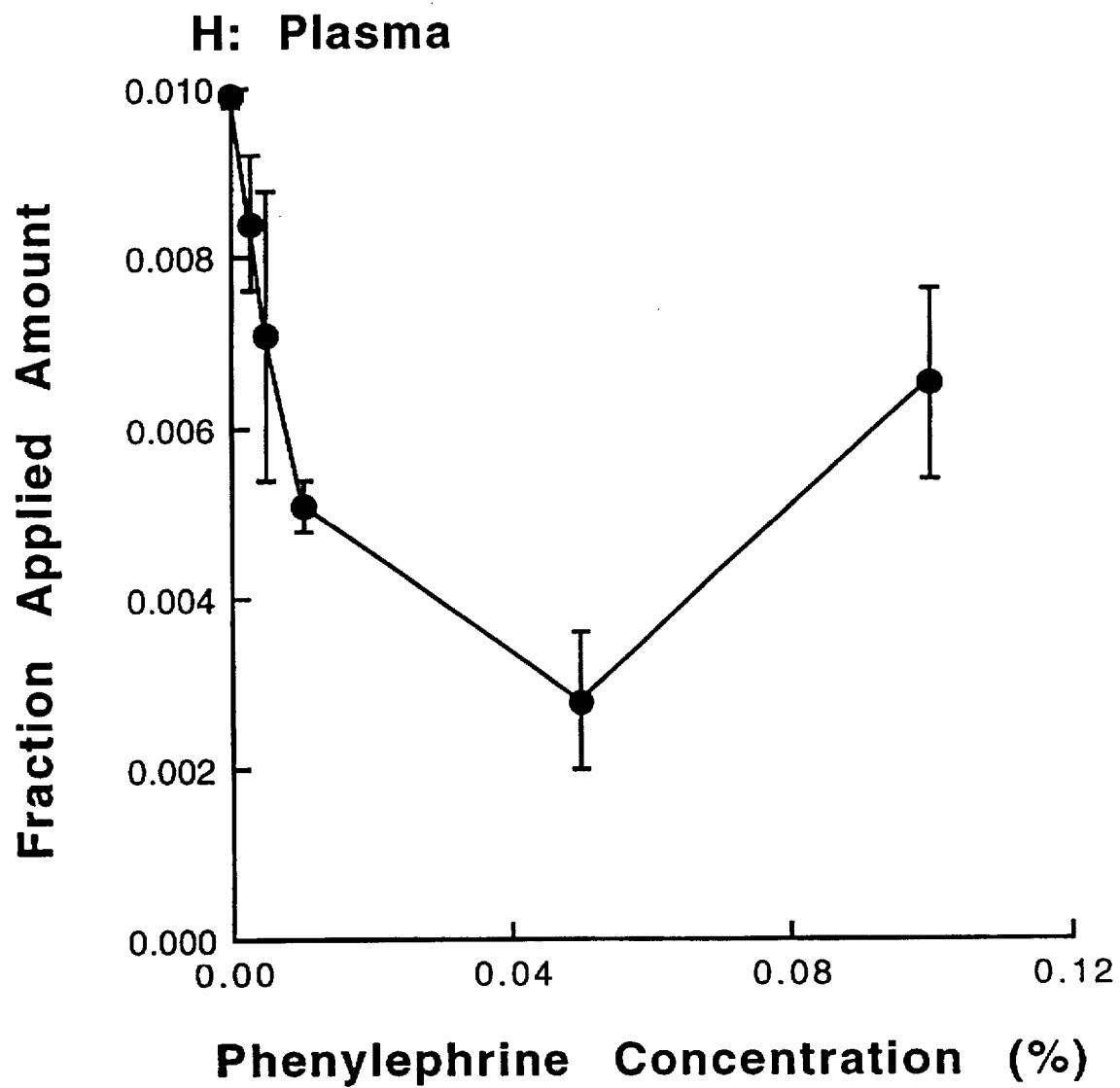
FIG. 2h shows the relationship between the phenylephrine concentration and the concentration of salicylic acid (expressed as a fraction of initial donor concentration) in plasma after dermal application.

FIGS. 2a–g show fraction (of initial concentration) of salicylic acid in underlying tissues, contralateral tissues and plasma (FIGS. 2h) at various PE concentrations after dermal application. The concentrations of salicylic acid in underlying tissues (except for fat pad) increase with increase in concentration of PE up to 0.01%. At higher PE concentrations, the concentrations of salicylic acid approach a constant value. The systemic salicylic acid blood levels show a gradual decline with increasing phenylephrine concentration (FIG. 2h). The corresponding salicylic acid concentrations in the corresponding tissues from the control contralateral site also decreased with increasing phenylephrine concentrations suggesting decreased systemic availability and distribution of salicylic acid (FIG. 2a–g). However, at a PE concentration of 0.1%, plasma salicylic acid levels (FIG. 2h) and salicylic acid levels in contralateral tissues (FIG. 2a–g) show a sudden increase. The changes in contralateral salicylic acid concentrations are most likely due to central cardiovascular effects associated with the systemic absorption of phenylephrine after application of very high concentrations.

The concentrations of tritiated water and lidocaine in the tissues below the application area also increased in the presence of phenylephrine (FIGS. 3 & 4) whereas those in the plasma and contralateral tissues decreased. Riviere et al have recently shown that cointophoresis of lidocaine and norepinephrine (a vasoconstrictor) increased local concentrations of lidocaine in the skin up to a depth of 3 mm as described in Pharm. Res. (1992) 9 211–214. A decrease in the plasma levels of lidocaine in the presence of phenylephrine after subcutaneous administration in rats has been shown in Canepa et al as described in Plast. Reconstr. Surg. (1988) 81 554–560. In the presence of phenylephrine, the concentrations of solutes in underlying tissues will always be intermediate between those obtained for normal blood supply and no blood supply (sacrificed animal). The sacrificed animal represents an extreme case of vasoconstriction where there is essentially no blood flow and any absorbed solute localises in the tissues below the applied site by simple diffusion in and between tissues.

EXAMPLE 2

We have been able to show that following topical application of the vasodilator glyceryl trinitrite (GTN) to the rat paw in anaesthetised animals we can significantly increase the underlying tissue concentration of topically coadministered $^3$H-water. Previous work in this laboratory has demonstrated the blood flow dependence of the dermal absorption of water and we believe that the experimental data presented below supports the claims made in this invention.

Male Wistar rats (348±20 g) were anaesthetised i.p. with sodium pentobarbitone (60 mg/kg) and laid abdomen down on a heating pad (37° C.) with the left hindleg extending over the edge of the pad. The left hind foot was cleaned with cotton wool swabs soaked in a dilute solution of ethanol then dried. The foot was then immersed, to a standard position marked on the ankle joint, in 2 ml of vehicle solution (30% propylene glycol/30% ethanol/40% water) containing $^3$H-water (Sigma, Australia) with (n=3) or without (n=3) 2% GTN (David Bull Laboratories Pty Ltd. Melbourne, Australia). Solutions were left in contact with the foot for 2 hours with 10 µl samples taken at time zero and at the end of the absorption period. After 2 hrs a blood sample was taken from the tail vein and animals were sacrificed by cervical dislocation whilst still anaesthetised. The rat paws were cleaned as previously to remove any excess radiolabelled solute from the surface. Skin from the upper part of the foot, the foot pad and foot muscles were dissected from each treated and contralateral paw, placed into preweighed scintillation vials, solubilised with NCS (Amersham, Australia) and counted for radioactivity, along with the 10 µl solution samples, following the addition of the appropriate scintillation cocktail. Statistical analysis was performed using a Student unpaired t-test, with significance taken at the P<0.05 level.

Figure 5:
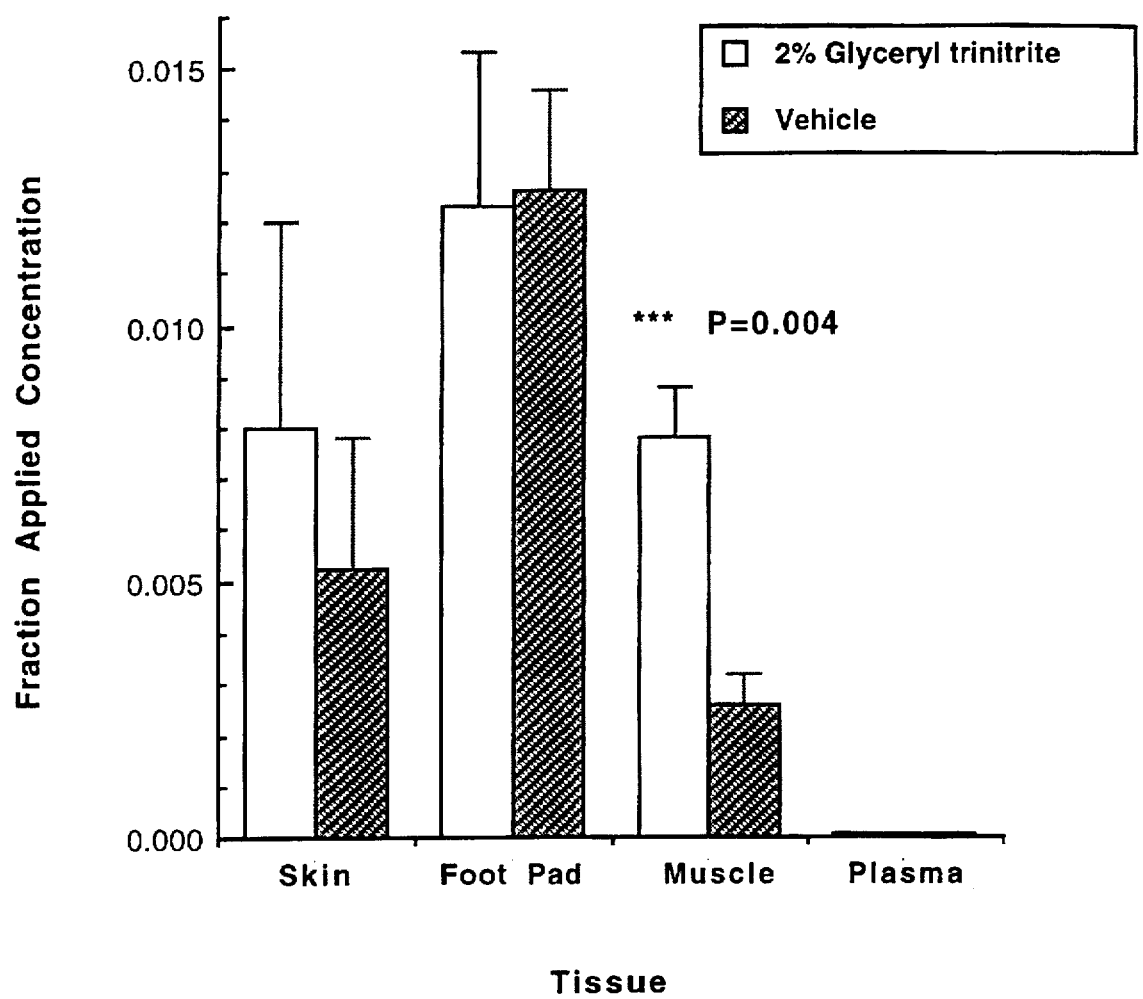
FIG. 5 shows the tissue concentrations of $^3$H-water after topical application in various locations, wherein keys (■) and (□) indicate control vehicle and 2% glyceryl trinitrite, respectively.

As shown in FIG. 5, there was a significant increase in the plasma concentration of water in the presence of GTN (P=0.046).

The tissue concentrations of water presence and absence of 2% GTN is shown in FIG. 5. The vasodilator caused a highly significant increase in the concentration of water in the deeper foot muscles, however, there was no significant change in the concentration of solute in the outer skin or foot pad of the rat paw in the presence of 2% GTN.

GTN is a potent vasodilator known to traverse the skin barrier and has been available commercially in topical preparations for its antianginal properties for many years. In Example 2 we used a 2% solution of GTN to determine whether local vasodilation could increase tissue perfusion and subsequent absorption of topically applied solutes. We have previously shown that the absorption of water is dependent on tissue perfusion rate, with reductions in blood flow causing significant reductions in absorption from dermal and subcutaneous sites. The increase in water plasma concentration in the presence of 2% GTN reflects the increased absorption of the solute into the rat paw.

The highly significant increase in water concentration in the muscle layers of the foot, and not the upper skin or foot pad areas, suggests that vasodilation is increasing the surface area of blood vessel available for absorption, and that once in the plasma the increase in local tissue perfusion causes increased transfer into the deeper tissues. The increased plasma concentrations of water also caused a significant increase in the concentration of water in the upper skin and muscle tissues of the contralateral limb, though not in the foot pad. This finding probably reflects the amount of blood perfusion to the upper skin and muscle areas of the paw compared to the foot pad with the increased concentrations achieved in the plasma.

EXAMPLE 3

Example 3 shows how alterations in blood flow can modify the absorption of a topically applied therapeutic agent. Thus more specifically this example shows increasing tissue perfusion rates (as would be achieved by vasodilators) modifies the absorption of dermally applied 3H-water. For the sake of convenience in the rates the outer stratum or epidermis has been stripped from the rat.

Example 3 therefore specifically demonstrates how alterations in tissue perfusion or tissue blood flow modify the absorption and tissue distulation of therapeutic agents and this illustrates the broad ramifications of the present invention.

Effect of Perfusion Flow Rate on the Transdermal Absorption of 3H-Water in the Perfused Rat Hindlimb The following experiment was designed to determine the effect of changes in tissue blood flow (perfusion) on the transdermal absorption and subsequent tissue distribution of 3H-water.

Rat hindlimb perfusions

Hindlimb perfusions: Briefly, rats (male Wistar 280–340 g) were anaesthetised with sodium pentobarbitone 60 mg/ig i.p., the abdomen opened and the right femoral artery cannulated (PE50) via the aorta. A second cannula (PE205) was placed in the dorsal vena cava, and the hindlimb perfused in a humidicrib at 37° C. with oxygenated (95%$O_2$/5%$CO_2$) Krebs Heinseleit Ringer (mM: NaCl 118, KCl 4.74, $KH_2PO_4$ 1.18, $MgSO_4.7H_2O$ 0 1.18 $CaCl_2.2H_2O$ 2.54, $NaHCO_3$ 25, Glucose 11.1;pH 7.4, 37° C.), containing 4% bovine serum albumin (Fraction V, Sigma). Once the perfusions were established rats were sacrificed by creating a pneumothorax and turned over so that cells could be attached to the outer thigh of the perfused limb. The pressure of the inflowing perfusate was continuously monitored, mean pressures were in the order of 30 and 40 mmHg at 4 and 8ml/min respectively. The perfused preparation is stable for up to 2 hrs, as validated by testing inflowing and outflowing perfusate samples for pH, dissolved oxygen concentrations, together with various enzyme and ion concentrations. The perfusion flow rates were controlled by a graduated peristaltic pump, and were measured at the beginning and end of each experiment.

Passive dermal absorption studies

Glass diffusion cells (8 cm high, 1.8 cm internal diameter, 2.54 $cm^2$ skin application area), were fixed to the skin on the outer thigh of the perfused hindlimb with adhesive. The application area on the hindlimb was first depilated with commercial Nair™ hair-removal cream and the epidermis removed using a dermatome before the perfusion was established. Solutions (2 ml) containing trace amounts of the radiolabelled $^3$H-water (Sigma Chemical Co, Australia), in phosphate buffered saline (pH 7.4, 37° C.) were introduced into the cell at time 0. Absorption studies were conducted for 90 minutes, after which time the cell contents were drawn out with a pipette, the cell removed and the tissues from beneath the position of the cell sequentially dissected into preweighed vials for weight determination, solubilisation and liquid scintillation counting.

Results

Topically applied solutes penetrate the skin and reach underlying tissues at rates determined by a number of factors, of principal importance is their chemical structure and the rate at which they are removed by the local blood supply. Water An increase in clearance from the dermal cell with perfusion flow rate was shown (p<0.05, Student t test), a 31% increase in clearance occurring as the perfusion flow rate was raised from 4 ml/min to 8 ml/min. The tissue concentrations of water also had a great dependence on perfusion flow rate. The actual tissue levels of water measured directly beneath the application site are shown in the attached figure. Tissue concentrations were statistically lower in the dermis (2 mm) (p<0.05) and superficial muscle layer (5 mm)(p<0.05) at the higher flow rate. These results are consistent with an increased clearance of water from the various tissues into the perfusate at the higher flow rate, as distinct from the clearance of water by diffusion into deeper tissues. At the lower flow rate higher concentrations of water are found in the deeper muscle layers. This deeper penetration shows that the dermal vasculature is not acting as a near perfect sink and that certain solutes, as demonstrated clearly by the present data, can bypass this sink and diffuse into deeper tissue layers.

From the foregoing, it therefore will be appreciated that advantages of the invention include the following:

(i) the technique of the present invention facilitates the administration of a vaso-active agent to targeted locations beneath the stratum corneum in an appropriate concentration;

(ii) the technique of the present invention allows for a particular location under the stratum corneum to be targeted for delivery of appropriate concentration of vaso-active agent to modify local perfusion and/or concentration of the therapeutic agent in body fluid such as serum adjacent the administration site of the therapeutic agent and/or vaso-active agent;

(iii) the technique of the present invention can be utilised in relatively inaccessible locations such as between the toes, under the arms or on the nose;

(iv) the technique of the present invention can be utilised for a prolonged period of time e.g. for 2–12 hours;

(v) the concentration of therapeutic agent can be controlled to avoid systemic side effects;

(vi) the use of the vaso-active agent can also be controlled in appropriate concentrations to avoid side effects e.g. ischaemia in the use of vaso-constrictors and for more efficient control of topical therapy; and (vii) the technique can have repeated application without detriment to the patient.

TABLE 1

Effect of phenylephrine on dermal clearance of tritiated water and lidocaine (Mean ± S.D.).

| Treatment | Water (ml/hr) | Lidocaine (ml/hr) |
|---|---|---|
| Control | 1.10 ± 0.24 | 0.51 ± 0.15 |
| Phenylephrine (1:20000) | 0.53 ± 0.05 | 0.37 ± 0.01 |
| Phenylephrine (1:5000) | 0.40 ± 0.02 | 0.34 ± 0.02 |
| Sacrificed | 0.36 ± 0.02 | 0.33 ± 0.06 |

Figure Legends

FIG. 1—Effect of phenylephrine concentration on salicylic acid clearance after application to rat dermis.

FIG. 2 (a–h)—Effect of phenylephrine concentration on the concentration of salicylic acid (expressed as fraction of initial donor concentration) in underlying tissues (●), contralateral tissues (○) and plasma (FIG. 4h) after dermal application. Values are reported as mean±sd.

Figure 3:
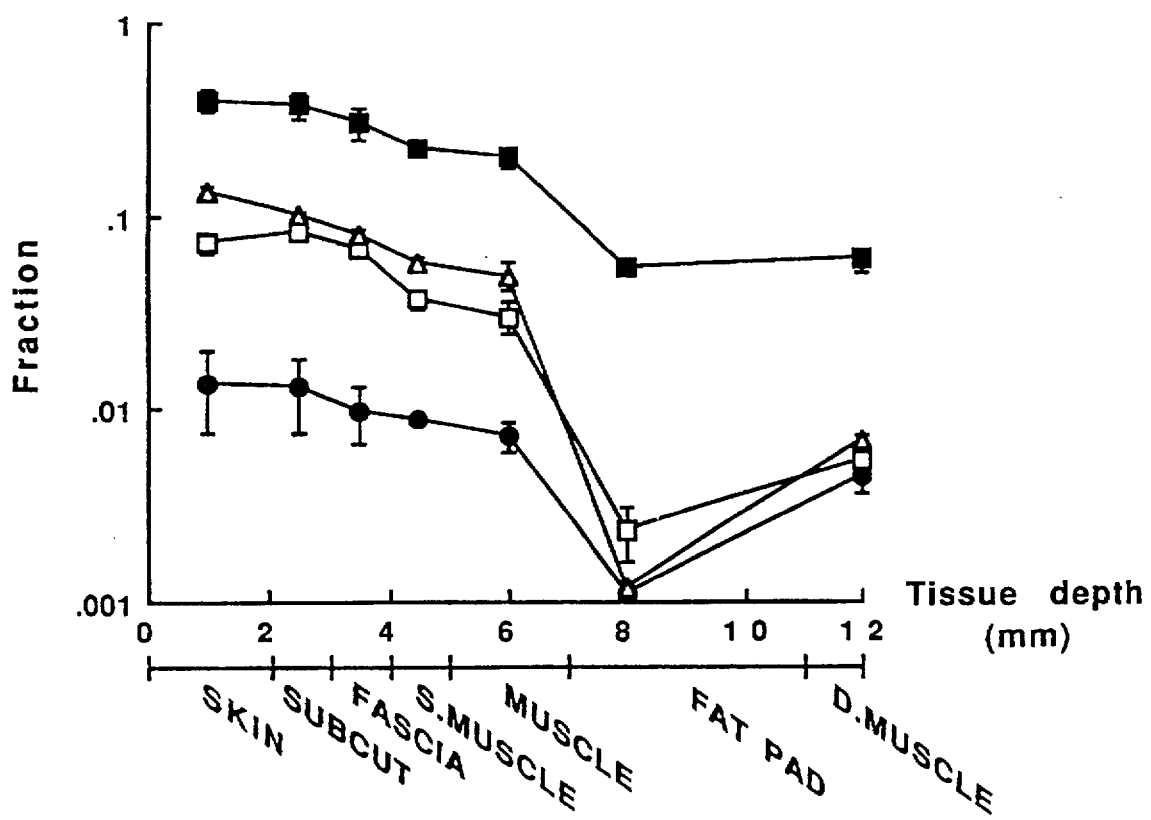
FIG. 3 shows the relationship between the tissue depth below a dermal application site and the concentrations of tritiated water (expressed as fractions of initial donor concentration), wherein keys (■), (△), (□), and (●) indicate sacrificed animal, phenylephrine concentration (1:5000), phenylephrine concentration (1:20000), and anaesthetized animal in the absence of phenylephrine, respectively.

FIG. 3—Concentration of tritiated water (as a fraction of initial donor concentration) in tissues below a dermal application site. Key: (■) sacrificed animal, (△) PE conc. (1:5000), (□) PE conc. (1:20000), (●) anaesthetised animal in absence of PE. Values are reported as means±sd.

Figure 4:
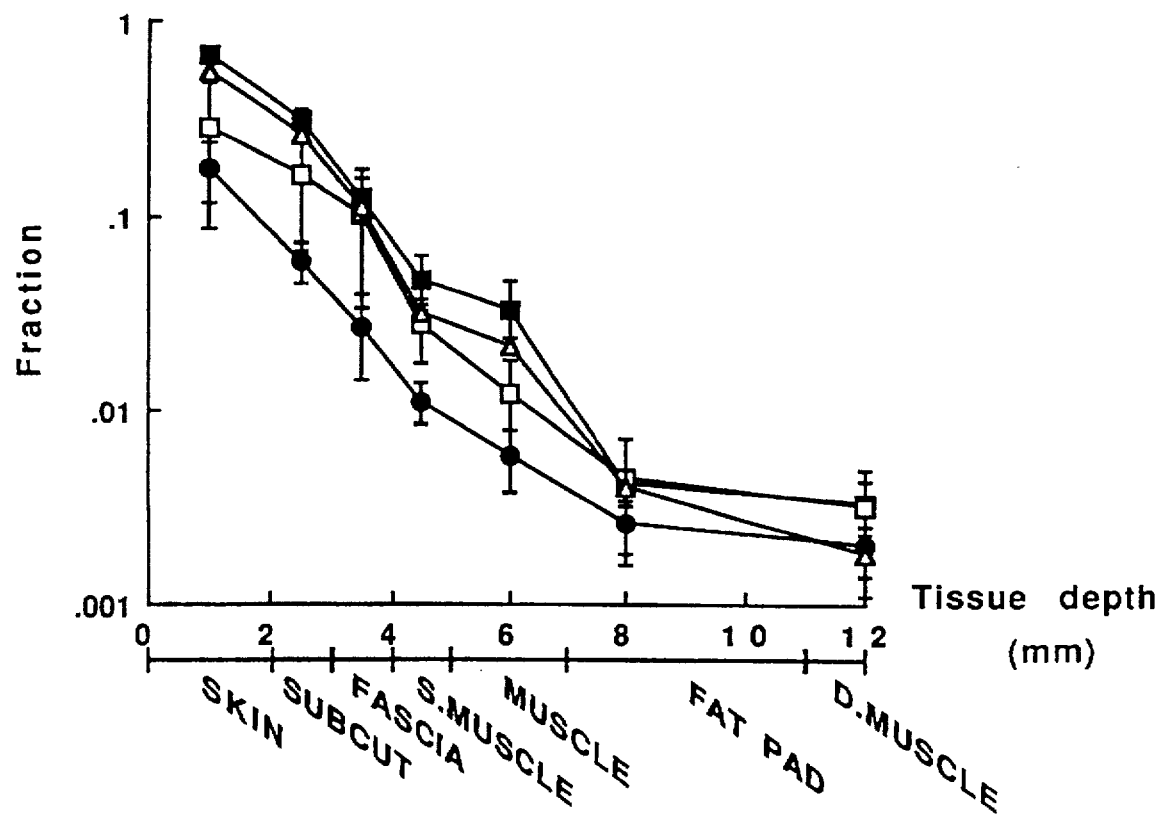
FIG. 4 shows the relationship between the tissue depth below a dermal application site and the concentrations of lidocaine (expressed as fractions of initial donor concentration), wherein keys (■), (△), (□), and (●) indicate sacrificed animal, phenylephrine concentration (1:5000), phenylephrine concentration (1:20000), and anaesthetized animal in the absence of phenylephrine, respectively.

FIG. 4—Concentration fraction of lidocaine (as a fraction of initial donor concentration) in tissues below a dermal application site. Key: (■) sacrificed animal, (△) PE conc. (1:5000), (□) PE conc. (1:20000), (●) anaesthetised animal in absence of PE. Values are reported as mean±sd.

FIG. 5—Tissue concentrations of 3H-Water following topical application. Key: (□) 2% Glyceryl trinitrite, (■) Control Vehicle.

Figure 6:
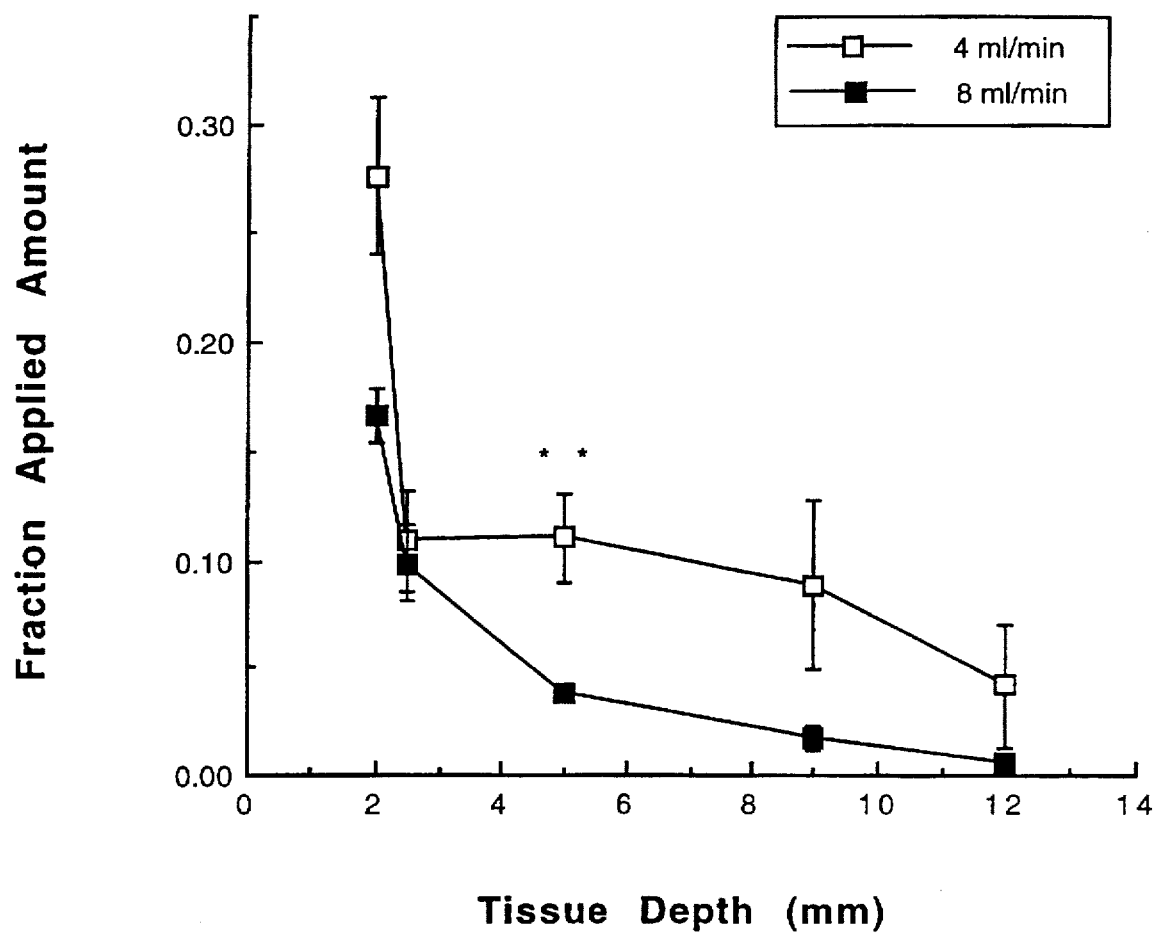
FIG. 6 shows the relationship between the tissue concentration of $^3$H-water and the tissue depth when perfusion was performed at a perfusion flow rate of 4 ml/min (□) or 8 ml/min (■).

FIG. 6—Effect of perfusion flow rate tissue concentration of 3H-Water after dermal application in the perfused rat hindlimb. Key: (□) 4 ml/min, (■) 8 ml/min.

We claim:

1. A method of topical and/or transdermal administration of a vaso-active agent in combination with a therapeutic agent to increase local perfusion and/or concentration of the therapeutic agent adjacent to an administration site of the vaso-active agent, said therapeutic agent being selected from the group consisting of an anti-inflammatory agent and an anesthetic, comprising the steps of:

(i) selecting a targeted location under the stratum corneum from the group consisting of dermis epidermis, subcutaneous tissue, fascia, smooth muscle, muscle, fat pad, deep muscle joint tissue, bone, and plasma;

(ii) correlating the concentration of the vaso-active agent topically and/or transdermally administered with the degree of penetration of the therapeutic agent to the targeted location adjacent to the administration site of the vaso-active agent, relative to an initial concentration of the therapeutic agent which is applied topically or locally;

determining a concentration of the vaso-active agent to increase local perfusion and/or concentration of the therapeutic agent adjacent to the administration site of the vaso-active agent; and (iv) topically and/or transdermally administering the vaso-active agent, using at least the concentration of said vaso-active agent determined in step (iii), in combination with the therapeutic agent at said initial concentration, wherein the vaso-active agent is administered separately to or in combination with the therapeutic agent.

2. A method of topical and/or transdermal administration of a vase-active agent in combination with a therapeutic agent to increase local perfusion and/or concentration of the therapeutic agent adjacent to an administration site of the vaso-active agent, said therapeutic agent being selected from the group consisting of an anti-inflammatory agent and an anesthetic, comprising the steps of:

(i) selecting a targeted location under the stratum corneum from the group consisting of dermis, epidermis, subcutaneous tissue, fascia, smooth muscle, muscle, fat pad, deep muscle, joint tissue, bone, and plasma;

(ii) correlating the concentration of a first vaso-active agent topically and/or transdermally administered with the degree of penetration of the therapeutic agent to the targeted location adjacent to the administration site of the first vaso-active agent, relative to an initial concentration of the therapeutic agent which is applied topically or locally;

(iii) determining a concentration of the first vaso-active agent to increase local perfusion and/or concentration of the therapeutic agent adjacent to the administration site of the first vaso-active agent; and (iv) topically and/or transdermally administering a second vaso-active agent different from the first vaso-active agent utilized in step (iii) wherein the concentration of the second vaso-active agent is determined from the equation:

$$\text{CONCENTRATION OF SECOND VASO-ACTIVE AGENT} = \frac{\text{EQUIVALENT CONCENTRATION OF FIRST VASO-ACTIVE AGENT} \times \text{POTENCY OF SECOND VASO-ACTIVE AGENT}}{\text{POTENCY OF FIRST VASO-ACTIVE AGENT}}$$

wherein said second vaso-active agent is administered in at least the concentration determined from said equation in combination with the therapeutic agent at said initial concentration, wherein the vaso-active agent is administered separately to or in combination with the therapeutic agent.

3. A method as claimed in claim 1 wherein the therapeutic agent is administered in combination with the vaso-active agent.

4. A method as claimed in claim 1 wherein the therapeutic agent is administered separately to the vaso-active agent.

5. A method as claimed in claim 4 wherein the therapeutic agent is administered at the same site as the vaso-active agent.

6. A method as claimed in claim 5 wherein the therapeutic agent is administered adjacent the site of administration of the vaso-active agent.

7. A method as claimed in claim 4 wherein the therapeutic agent and the vaso-active agent are separately administered within a time interval effective to increase in local perfusion and/or concentration of the therapeutic agent in body fluid in tissues adjacent to the administration site of the vaso-active agent.

8. A method as claimed in claim 7 wherein the short time interval is 15–60 minutes.

9. A method as claimed in claim 1 wherein the vaso-active agent is a vasodilator.

10. A method as claimed in claim 1 wherein the vaso-active agent is a vasoconstrictor.

11. A composition for topical and/or transdermal administration comprising a vaso-active agent in combination with a therapeutic agent to increase local perfusion and/or concentration of the therapeutic agent at or adjacent an administration site of the vaso-active agent, said therapeutic agent being selected from the group consisting of an anti-inflammatory agent and an anesthetic, wherein the concentration of said vaso-active agent and the concentration of said therapeutic agent are sufficient to increase local perfusion and/or concentration of the therapeutic agent at or adjacent a targeted location under the stratum corneum, said location being selected from the group consisting of the dermis, epidermis, subcutaneous tissue, fascia, smooth muscle, muscle, fat pad, deep muscle, joint tissue, bone, and plasma.

12. A composition as claimed in claim 11 wherein the vaso-active agent is a vasodilator.

13. A composition as claimed in claim 11 wherein the vaso-active agent is a vasoconstrictor.

14. A composition as claimed in claim 11 further including a vehicle or excipient which is a non-toxic non-aqueous compound.

15. A composition as claimed in claim 11 wherein the vehicle or excipient is a paraffin.

16. A composition as claimed in claim 12 comprising 0.5%–5.0% of vaso-active agent.

17. A method as claimed in claim 2 wherein the therapeutic agent is administered in combination with the vaso-active agent.

18. A method as claimed in claim 2 wherein the therapeutic agent is administered separately from the vaso-active agent.

19. A method as claimed in claim 18 wherein the therapeutic agent is administered at the same time as the vaso-active agent.

20. A method as claimed in claim 19 wherein the therapeutic agent is administered adjacent the site of administration of the vaso-active agent.

21. A method as claimed in claim 18 wherein the therapeutic agent and the vaso-active agent are separately administered within a time interval effective to increase in local perfusion and/or concentration of the therapeutic agent in body fluid in tissues adjacent to the administration site of the vaso-active agent.

22. A method as claimed in claim 21 wherein the short time interval is 15 to 60 minutes.

23. A method as claimed in claim 2 wherein the vaso-active agent is a vasodilator.

24. A method as claimed in claim 2 wherein the vaso-active agent is a vasoconstrictor.

* * * * *